(12) United States Patent
Wang et al.

(10) Patent No.: US 9,070,184 B2
(45) Date of Patent: Jun. 30, 2015

(54) COLOR FLOW GAIN ADJUSTMENT METHOD AND DEVICE

(71) Applicant: Shenzhen Mindray Bio-Medical Electronics Co., Ltd., Shenzhen (CN)

(72) Inventors: Yan Wang, Shenzhen (CN); Xiangzuo Zheng, Shenzhen (CN); Yonggiang Dong, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/170,410

(22) Filed: Jan. 31, 2014

(65) Prior Publication Data

US 2014/0148700 A1  May 29, 2014

Related U.S. Application Data

(63) Continuation of application No. 13/335,723, filed on Dec. 22, 2011, now Pat. No. 8,649,586.

(30) Foreign Application Priority Data

Dec. 30, 2010 (CN) .......................... 2010 1 0615840

(51) Int. Cl.
*G06K 9/00* (2006.01)
*G06T 7/00* (2006.01)
*A61B 8/06* (2006.01)
*A61B 8/14* (2006.01)
*A61B 8/08* (2006.01)
*A61B 8/00* (2006.01)

(52) U.S. Cl.
CPC ................. *G06T 7/0012* (2013.01); *A61B 8/06* (2013.01); *A61B 8/14* (2013.01); *A61B 8/488* (2013.01); *A61B 8/5207* (2013.01)

(58) Field of Classification Search
CPC .................................... A61B 8/00; G06T 7/00
USPC ......... 382/128, 129, 130, 131, 132, 133, 134; 378/4, 8, 21–27, 101, 901; 600/407, 600/410, 411, 425, 427, 443
See application file for complete search history.

(56) References Cited

U.S. PATENT DOCUMENTS

| | | | | |
|---|---|---|---|---|
| 5,865,750 | A * | 2/1999 | Hatfield et al. | 600/443 |
| 7,613,335 | B2 * | 11/2009 | McLennan et al. | 382/128 |
| 7,648,461 | B2 * | 1/2010 | Thiele | 600/453 |

* cited by examiner

*Primary Examiner* — Abolfazl Tabatabai
(74) *Attorney, Agent, or Firm* — Kory D. Christensen; Stoel Rives LLP (57) ABSTRACT

A color flow gain adjustment method and device, and a color ultrasound imaging system using the device are disclosed.

20 Claims, 6 Drawing Sheets

COLOR FLOW GAIN ADJUSTMENT METHOD AND DEVICE

CROSS-REFERENCE TO RELATED APPLICATION(S)

This application claims the benefit of Chinese Patent Application No. 201010615840.0, filed on Dec. 30, 2010, which is incorporated herein by reference in its entirety.

TECHNICAL FIELD

The following disclosure relates to the field of ultrasonic imaging and, more particularly, to a color flow gain adjustment method and device used in an ultrasonic imaging system.

DETAILED DESCRIPTION

Color Flow Mapping (CFM) is widely applied in nondestructive detection and measurement of human blood flow. Using CFM, hemodynamic characteristics in a specific area of a human body can be observed, so that a speed, intensity, degree of disorder, and/or spatial distribution of the blood flow can be determined.

Figure 1:
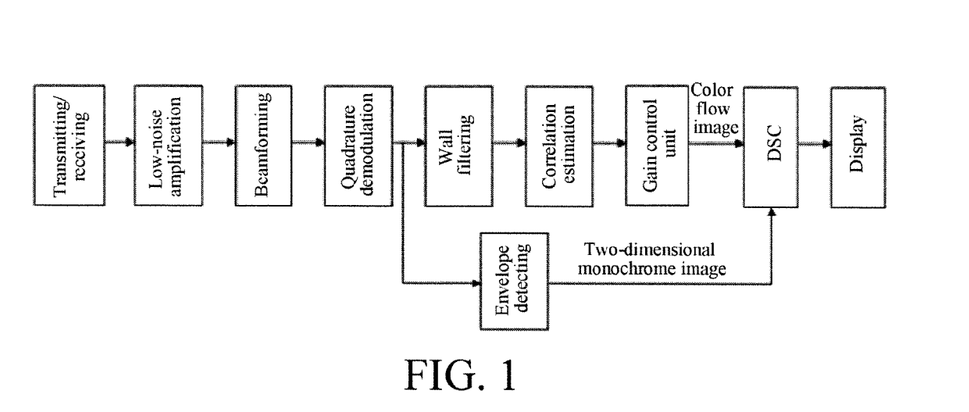
FIG. 1 is a schematic view of a typical CFM system.

FIG. 1 is a schematic block diagram of a typical CFM system. A transducer transmits a series of ultrasonic signals to a human body, and the ultrasonic signals are received by the transducer after being scattered by human tissues and blood flows. The transducer converts the received ultrasonic signals into electric signals and acquires in-phase (I) and quadrature (Q) baseband signals after low-noise amplification, beamforming, and quadrature demodulation. Envelope detection may be performed on the quadrature baseband signals to generate a two-dimensional monochrome image signal of the human tissues. Additionally, wall filtering may be performed on the quadrature baseband signals to filter out tissue and wall echo signals of very low frequencies so as to acquire Doppler signals including only flow movement information. Autocorrelation estimation processing is performed on the signal after the filtering to acquire, among other things, an average speed value, energy, and variance of the Doppler signal. After being processed by a Digital Scan Converter (DSC), dynamics information, such as the speed, energy, and variance of the flow, is displayed in real time according to the two-dimensional distribution of the flow in the form of a two-dimensional color flow image.

During CFM, a gain control unit, as shown in FIG. 1, may be used for adjusting color gain in order to improve the sensitivity of flow signal detection. Due to individual differences between patients, color gain is a parameter most frequently adjusted by a clinician during clinical diagnosis. By adjusting the color gain, the clinician improves color flow sensitivity as much as possible while suppressing background noise caused by higher gain levels as much as possible.

An operation panel of a conventional color Doppler diagnostic ultrasound apparatus always includes a knob for adjusting the color gain. Each time the knob is turned, the gain level increases or decreases by a certain value to reach a next level preset in the system. Although steady, the operation is time-consuming. Especially when a large difference lies between the current level and a target level, an operator needs to adjust the knob manually multiple times before reaching an expected parameter value. Therefore, an automatic gain optimization technology for determining an optimum gain level that incurs no noise while ensuring flow sensitivity would be an important feature.

Figure 2:
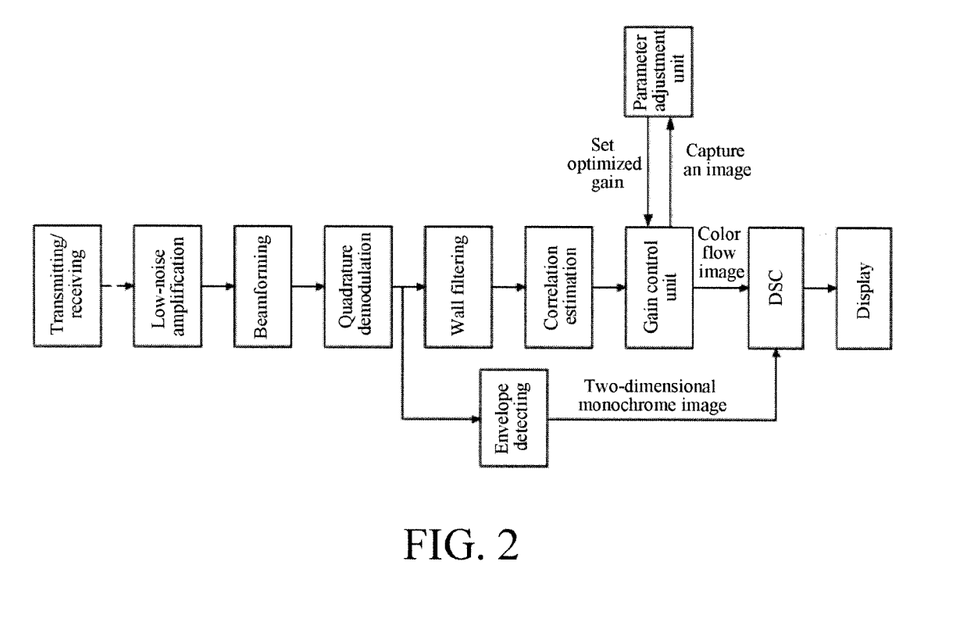
FIG. 2 is a schematic view of a typical CFM gain automatic optimization system.

As shown in FIG. 2, a typical CFM system having an automatic gain optimization function includes an additional parameter adjustment unit compared with that shown in FIG. 1. If a user enables the automatic gain optimization function of the CFM system, the parameter adjustment unit is triggered. The parameter adjustment unit acquires color flow images within a certain period of time, acquires an adjusted color gain level through analysis, and feeds back the level to a gain control unit. However, conventional techniques for automatic gain optimization have problems with low-speed flow sensitivity.

The present disclosure is directed to a color flow gain adjustment method and device in which CFM gain parameters are optimized automatically, thereby simplifying manual gain adjustment for a clinician and improving diagnostic efficiency.

In one embodiment, a color flow gain adjustment method includes: storing ultrasound image data within a preset time; calculating an abnormal pixel point ratio in a selected area of the stored ultrasound image data; and adjusting color gain based on a result of a comparison between the abnormal pixel point ratio and a preset threshold.

Similarly, a color flow gain adjustment device may include: a storage module for storing ultrasound image data within a preset time; a logic module for calculating an abnormal pixel point ratio in a selected area of the stored ultrasound image data; and an adjustment module for adjusting color gain based on a result of a comparison between the abnormal pixel point ratio and a preset threshold.

In one embodiment, a color ultrasound imaging system is provided, which includes a transducer and a signal processing device. The transducer is for transmitting an ultrasonic signal and receiving an ultrasonic echo signal. The signal processing device is for performing signal processing on the ultrasonic echo signal received by the transducer to acquire ultrasound image data. The system further includes a color flow gain adjustment device as described herein.

For convenience of description, the following basic concepts are elaborated first.

(1) Cardiac cycle: According to movement characteristics of human blood flows, in order to completely acquire a movement state of blood flows, a time of at least one cardiac cycle is required. A cardiac cycle normally involves multiple color images.

(2) Blood flow: Normally, a pixel point having high energy and a high speed is regarded as a normal flow.

(3) Noise: Normally, a pixel point having low energy and a large variance is regarded as background noise.

Figure 3:
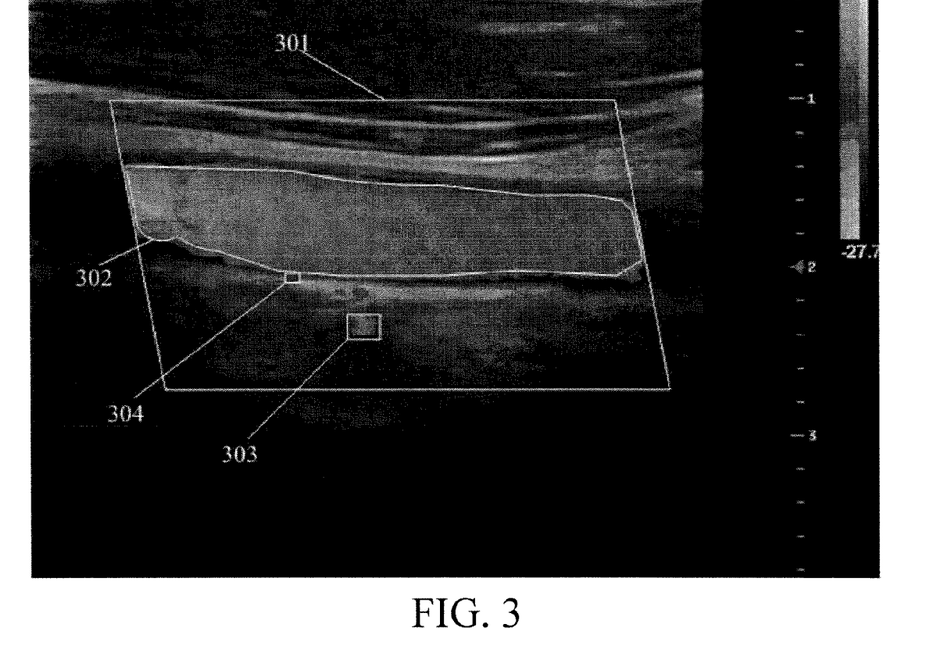
FIG. 3 is a schematic view of a carotid flow image having an overflow point and a noise point.

(4) Overflow: Normally, a strong flow signal is not likely to occur at positions having strong tissue echo signals on a two-dimensional monochrome image. For example, where a flow occurs at positions of strong echoes of upper and lower walls of a carotid artery, this is referred to an overflow. For more clear illustration, FIG. 3 is a carotid flow image. In the figure, a parallelogram frame 301 represents a sampling frame, an irregular frame 302 represents a normal flow, a rectangular frame 303 represents noise, and a rectangular frame 304 represents an overflow.

(5) Energy threshold of a gain level: Energy of a Doppler signal capable of being displayed corresponding to each gain level built into a system is calculated according to the gain level, and the energy is an energy threshold of the gain level.

According to the present disclosure, by analyzing ultrasound image data that is stored within a preset time and undergoes signal processing, an abnormal pixel point ratio is acquired, and a suitable level of color gain is determined according to a comparison of the ratio and a preset threshold.

Figure 4:
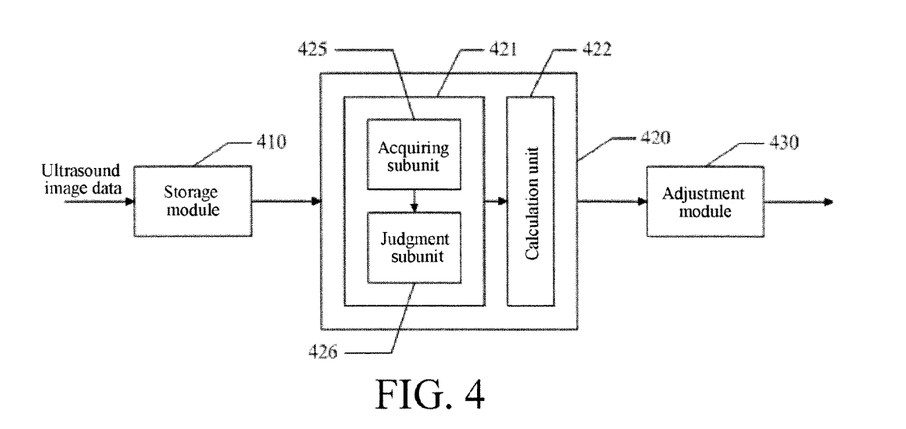
FIG. 4 is a schematic view of a color flow gain adjustment device according to an embodiment of the present disclosure.

FIG. 4 is a schematic view of an embodiment of a CFM gain adjustment device according to one embodiment. As shown in FIG. 4, the device includes: a storage module 410, a logic module 420, and an adjustment module 430. The storage module 410 is for storing ultrasound image data within a preset time. The logic module 420 is for calculating an abnormal pixel point ratio in a selected area of the stored ultrasound image data. The selected area may be an area covered by a sampling frame set by a user or another sampling area set, for example, by a system. The adjustment module 430 is for adjusting color gain based on a result of comparing the abnormal pixel point ratio and a preset threshold. In one embodiment, the abnormal pixel point ratio is compared with the preset threshold and a maximum abnormal pixel point ratio is selected from abnormal pixel point ratios smaller than the preset threshold. Color gain adjustment is performed according to a gain level corresponding to the maximum abnormal pixel point ratio.

In one embodiment, the logic module 420 includes an analysis unit 421 and a calculation unit 422. The analysis unit 421 is for determining abnormal pixel points in the selected area of the ultrasound image data according to a threshold value for each gain level built into the system based on the ultrasound image data. The calculation unit 422 is for calculating the abnormal pixel point ratio according to the determined abnormal pixel points so as to acquire the abnormal pixel point ratio corresponding to each of the gain levels of the system.

The analysis unit 421 may further include an acquiring subunit 425 and a judgment subunit 426. The acquiring subunit 425 is used to determine a speed, energy, brightness, and/or variance of each pixel point in the selected area of the ultrasound image data. The judgment subunit 426 is used to compare the speed, energy, brightness, and/or variance of each of the pixel points with a speed threshold value, energy threshold value, brightness threshold value, and/or variance threshold value, respectively, and judges whether the pixel point is an abnormal pixel point based on the comparison.

A color ultrasound imaging system according to one embodiment includes a transducer, a signal processing device, and a color flow gain adjustment device. The transducer is for transmitting an ultrasonic signal and receiving an ultrasonic echo signal. The signal processing device is for performing signal processing on the ultrasonic echo signal received by the transducer to acquire ultrasound image data.

FIG. 4 shows one embodiment of the color flow gain adjustment device. The signal processing device may use various known techniques to perform signal processing on the ultrasonic echo signal received by the transducer.

Figure 5:
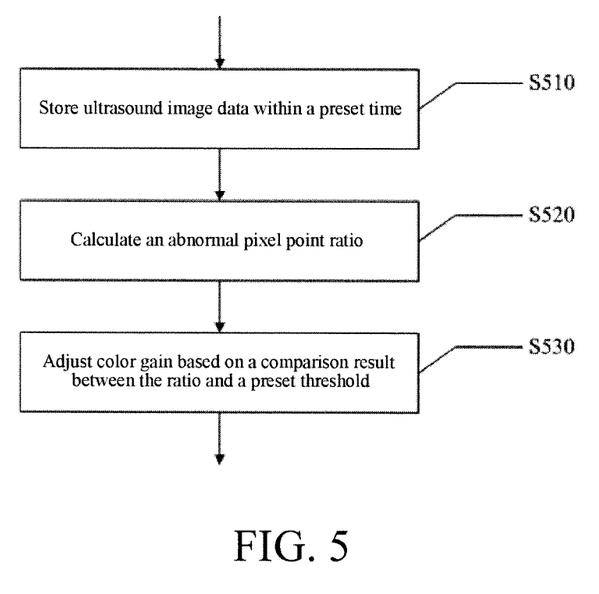
FIG. 5 is a schematic flow chart of a color flow gain adjustment method according to an embodiment of the present disclosure.

According to one embodiment, a method based on the color flow gain adjustment device, as shown in FIG. 5, includes the following steps.

In Step S510, ultrasound image data within a preset time is stored.

In one embodiment, a color gain automatic optimization function is started. After the function is started, the system automatically sets an energy threshold to 0, which is equivalent to setting a color gain level to the maximum, and then the ultrasound image data within the preset time is stored, as well as statistics related to the ultrasound image data in one embodiment. The ultrasound image data may include color flow image data and two-dimensional monochrome image data. The color flow image data may also include, but is not limited to, a speed diagram, an energy diagram, and a variogram. A memory stores at least one frame of color flow image data (including but not limited to a speed diagram, an energy diagram, and a variogram) and at least one frame of two-dimensional monochrome image data, which may be stored in the memory in the form of color flow movement parameters (such as a speed, an energy, and a variance) and a monochrome brightness value. The preset time for storage may be one cardiac cycle or a time set according to actual needs. In this embodiment, the preset time for storage is a cardiac cycle.

The system may also store preset threshold values. The preset threshold values are threshold values set in advance for performing cluster analysis on flows, noise points, and overflow points, including but not limited to threshold values related to a speed, an energy, a variance, a two-dimensional image brightness value, and other parameters. In this embodiment, the preset threshold values are determined with reference to normal flow parameter ranges. Specifically, a threshold value related to the speed is 0.2-1 times of a current speed level, a threshold value related to the variance is 0-0.4 times of a maximum variance of the current system, and a threshold value related to the energy is 0.25-1 times of maximum energy of the current system. A range of a threshold value of a brightness value of the two-dimensional monochrome image depends on the specific system and application mode, and is determined according to specific circumstances.

In Step S520, an abnormal pixel point ratio is calculated.

Step S520 may include the following sub-steps.

In a Step S521 (not shown), abnormal pixel points in a selected area of the ultrasound image are judged according to a preset threshold value at each of the gain levels built into the system based on the ultrasound image data in Step S510. Normally, the selected area is an area covered by a set sampling frame.

In a Step S522 (not shown), the abnormal pixel point ratio is calculated according to the judged abnormal pixel points, so that the abnormal pixel point ratio corresponding to each of the gain levels built into the system is acquired.

The preset threshold values may include a speed threshold value, an energy threshold value, a brightness threshold value, and/or a variance threshold value. The speed threshold value, the energy threshold value, and the variance threshold value may be determined by using the method in Step S510 for determining the preset threshold values, but the brightness threshold value may depend on the specific system and application mode, and is determined according to specific circumstances.

In Step S521, a speed, energy, and brightness and/or a variance of each pixel point in the selected area of the ultrasound image data are initially determined. The speed, energy, brightness, and/or variance of each of the pixel points are compared with the speed threshold value, energy threshold value, brightness threshold value, and/or variance threshold value, respectively, and then whether the pixel point is an abnormal pixel point or a normal pixel point is determined based on a result of the comparison.

Abnormal pixel points include overflow points and/or noise points. Abnormal pixel point ratios include an overflow ratio and/or a noise ratio. Normal pixel points include non-overflow points and/or flow points. Normal pixel point ratios include a non-overflow point ratio and/or a flow ratio. At least six situations may occur:

1) The abnormal pixel points include overflow points;
2) The abnormal pixel points include noise points;
3) The abnormal pixel points include overflow points and noise points;
4) The normal pixel points include non-overflow points;
5) The normal pixel points include flow points; and
6) The normal pixel points include non-overflow points and flow points.

For the aforementioned situations, the abnormal pixel point ratio may be calculated by using the following two methods.

In one method, the abnormal pixel point ratio is $$\text{Abnormal\_ratio} = \frac{N_{abnormal}}{N_{total}},$$

where Abnormal_ratio is the abnormal pixel point ratio, $N_{total}$ is the total number of pixel points in a selected area, and $N_{abnormal}$ is the total number of abnormal pixel points in the selected area.

In another method, the abnormal pixel point ratio is $$\text{Abnormal\_ratio} = \frac{N_{abnormal}}{N_{total} - N_{normal}} \text{ or Abnormal\_ratio} = \frac{N_{abnormal}}{N_{normal}},$$

where Abnormal_ratio is the abnormal pixel point ratio, $N_{total}$ is the total number of pixel points in a selected area, $N_{normal}$ is the total number of normal pixel points in the selected area, and $N_{abnormal}$ is the total number of abnormal pixel points in the selected area.

Generally, a pixel point having high energy and a high speed, as well as a weak tissue echo signal at a corresponding position, is a non-overflow flow. A pixel point having a high speed and high energy but a strong tissue echo signal at a corresponding position is regarded as an overflow flow. However, a strong flow signal is not likely to occur at positions having strong tissue echo signals on a two-dimensional monochrome image. For example, an overflow occurs at positions of strong echoes of the upper and lower walls of a carotid artery. Normally, a pixel point having high energy and a high speed is regarded as a normal flow, and a pixel point having low energy and a large variance is regarded as background noise. In addition, a pixel having high energy, a high speed, and a large variance is also regarded as a flow, and the flow is in a mixed state. Therefore, whether a pixel point is a flow point or a noise point is judged accordingly.

Assume that the speed threshold value includes an overflow speed threshold value, and the energy threshold value includes an overflow energy threshold value. If a speed of a pixel point is greater than the overflow speed threshold value, energy of the pixel point is greater than the overflow energy threshold value, and a brightness of the pixel point is greater than the brightness threshold value, the pixel point is judged as an overflow point; if a speed of a pixel point is greater than the overflow speed threshold value and a energy of the pixel point is greater than the overflow energy threshold value, but a brightness of the pixel point is less than the brightness threshold value, the pixel point is judged as a non-overflow point.

The speed threshold value may include a noise speed threshold value, the energy threshold value may include a noise energy threshold value, and the variance threshold value may include a noise variance threshold value. In one embodiment, if a speed of a pixel point is greater than the noise speed threshold value, an energy of the pixel point is less than the noise energy threshold value, and a variance of the pixel point is greater than the noise variance threshold value, the pixel point is judged to be a noise point; if a speed of a pixel point is greater than the noise speed threshold value, but a variance of the pixel point is less than the noise variance threshold value, the pixel point is judged to be a flow point.

After the overflow points, non-overflow points, noise points, and flow points are determined, it is assumed that the total number of all pixel points in the selected area of the image is $N\_{total}$, the total number of non-overflow points is $N\_{no\_overflow\_blood}$, the total number of overflow points is $N\_{overflow}$, the total number of noise points is $N\_{noise}$, and the total number of flow points is $N\_{blood}$. Accordingly, a formula for calculating the overflow ratio Overflow_ratio is $$\text{Overflow\_ratio} = \frac{N\_{overflow}}{N\_{total} - N\_{no\_overflow\_blood}},$$

$$\text{or Overflow\_ratio} = \frac{N\_{overflow}}{N\_{total}}, \text{ or Overflow\_ratio} = \frac{N\_{overflow}}{N\_{no\_overflow\_blood}};$$

a formula for calculating the noise ratio $$\text{Noise\_ratio is Noise\_ratio} = \frac{N\_{noise}}{N\_{total} - N\_{blood}},$$

$$\text{or Noise\_ratio} = \frac{N\_{noise}}{N\_{total}}, \text{ or Noise\_ratio} = \frac{N\_{noise}}{N\_{blood}}.$$

In Step S530, the color gain is adjusted based on a result of comparing the abnormal pixel point ratio and a preset threshold.

In one embodiment, the abnormal pixel point ratio is compared with the preset threshold, a maximum abnormal pixel point ratio is selected from abnormal pixel point ratios smaller than the preset threshold, and the color gain adjustment is performed according to the gain level corresponding to the maximum abnormal pixel point ratio.

Based on Step S520, the step involves at least the following three cases.

1) When the abnormal pixel point ratios include the overflow ratio and the preset threshold includes an overflow threshold, the overflow ratio is compared with the overflow threshold and a maximum overflow ratio is selected from overflow ratios smaller than the overflow threshold. A gain level corresponding to the maximum overflow ratio is an overflow gain level, and the system performs the color gain adjustment according to the overflow gain level. The overflow threshold may correspond to a maximum number of color overflow points that are allowed to appear in the selected area and may also be an empirical value.

In another embodiment, when each overflow ratio corresponding to a gain level is calculated, the overflow ratio is compared with the overflow threshold. If the overflow ratio is greater than the overflow threshold, the above step is performed to continue to calculate an overflow ratio of a next gain level; otherwise, calculation of an overflow ratio of another gain level is stopped, a gain level corresponding to the overflow ratio is used as an overflow gain level for output, and the system automatically adjusts the color gain according to the level.

2) When the abnormal pixel point ratios include the noise ratio and the preset threshold is a noise threshold, the noise ratio is compared with the noise threshold. A maximum noise ratio is selected from noise ratios smaller than the noise threshold, a gain level corresponding to the maximum noise ratio is a noise gain level, and the system performs the color gain adjustment according to the noise gain level. The noise threshold may correspond to a maximum number of color noise points that are allowed to appear in the selected area, and may also be an empirical value.

In another embodiment, when each noise ratio corresponding to a gain level is acquired by calculating, the noise ratio is compared with the noise threshold; if the noise ratio is greater than the noise threshold, the above step is performed to continue to calculate a noise ratio of a next gain level; otherwise, calculation of a noise ratio of another gain level is stopped, a gain level corresponding to the noise ratio is used as a noise gain level for output, and the system automatically adjusts the color gain according to the level.

3) When the abnormal pixel point ratios include an overflow ratio and a noise ratio and the preset thresholds include an overflow threshold and a noise threshold, the overflow threshold may correspond to a maximum number of color overflow points that are allowed to appear in the selected area (and may also be an empirical value). The noise threshold may correspond to a maximum number of color noise points that are allowed to appear in the selected area (and may also be an empirical value).

In this case, the overflow gain level and the noise gain level may be acquired according to 1) and 2) of this step, the overflow gain level is used as a lower limit of optimal gain levels, the noise gain level is used as an upper limit of the optimal gain levels, and a gain level between the lower limit of the optimal gain levels and the upper limit of the optimal gain levels is selected to perform the color gain adjustment. In this embodiment, the gain level is selected according to a preset rule, which includes a preset percentage; that is, according to a preset percentage, a suitable color gain level between the acquired upper limit and lower limit of the optimal levels is selected to perform the automatic gain adjustment.

In practice, options may be provided for a user to select a desired adjustment technique. In one embodiment, adjustment techniques may involve buttons or other controls. One adjustment technique may involve using only an overflow ratio to perform gain adjustment. Another adjustment technique may involve only a noise ratio to perform gain adjustment, and/or selecting gain between an overflow ratio and a noise ratio according to a preset value to perform adjustment, which may be selected by a user as needed.

More specific embodiments are provided below with reference to FIG. 6 to FIG. 8 to further illustrate gain control steps in a color flow gain adjustment method according to the present disclosure.

In one embodiment, color gain is controlled by controlling a ratio of the number of noise points that are allowed to appear in a sampling frame (that is, a selected area) to a non-flow space in the sampling frame. Such a process may include the following steps.

In Step A1, color gain is adjusted to a preset level to display noise points as much as possible.

In Step B1, a speed, variance, and energy of each image pixel point are taken and are used as a basis for judgment.

In Step C1, if a speed of an image pixel point is greater than a preset noise speed threshold value, an energy of the image pixel point is less than a preset noise energy threshold value, and a variance of the image pixel point is greater than a preset noise variance threshold value, the point is regarded as a noise point.

In Step D1, if a variance of an image pixel point is less than the preset noise variance threshold value and an energy of the image pixel point is greater than the preset noise energy threshold value, the point is regarded as a flow point.

In Step E1, according to each gain level built into a system, an energy threshold corresponding to the gain level is acquired.

In Step F1, whether a noise point signal can be displayed at the level is judged according to the energy threshold of the gain level, and the number of displayed noise points is counted.

In Step G1, a noise ratio is calculated.

In Step H1, a gain level corresponding to a noise ratio closest to a preset noise threshold is acquired according to the preset noise threshold, and the system performs an automatic adjustment according to the gain level.

Figure 6:
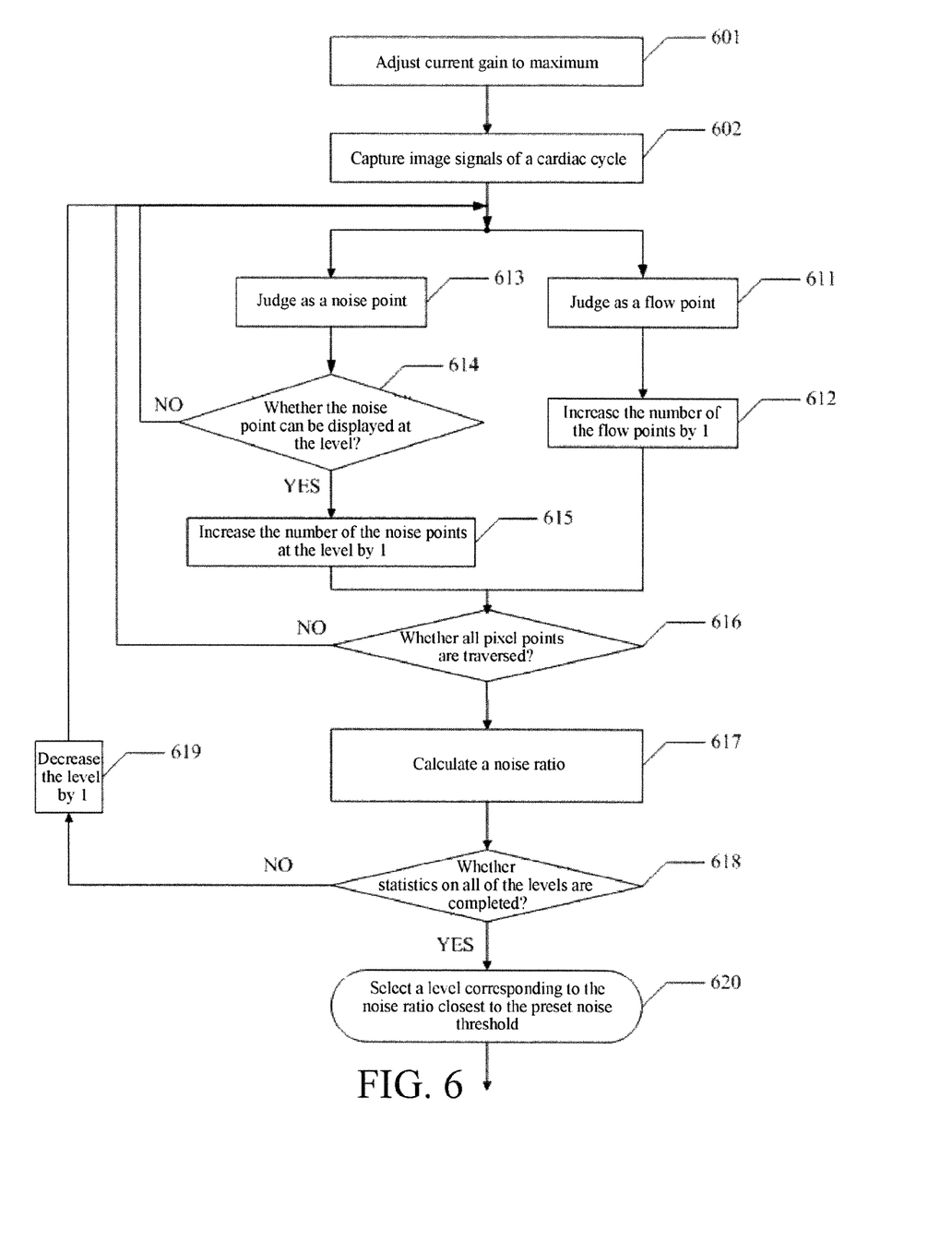
FIG. 6 is a schematic flow chart of suppressing overflows according to the embodiment shown in FIG. 5.

As shown in FIG. 6, an embodiment includes the following steps.

In Step 601, current gain is adjusted to maximum.

After a color gain automatic optimization function is started, the system automatically adjusts the color gain level to maximum, which is equivalent to setting the energy threshold to 0. The objective is to display the noise points as much as possible.

In Step 602, image signals of a cardiac cycle are captured.

According to movement characteristics of human blood flow, in order to acquire a movement state of blood flow completely, a time of at least one cardiac cycle is required. In this embodiment, statistics are taken on color flow image data and two-dimensional monochrome image data of one cardiac cycle, which are stored in a memory in the form of movement parameters (such as a speed, an energy, and a variance) and a monochrome brightness value.

In Step 611, a pixel point of a stored color flow image is judged as a flow point.

A specific judgment method is the same as that in Step S520.

In Step 612, the number of the flow points is increased by 1.

In Step 613, a pixel point of the stored color flow image is judged as a noise point.

In Step 614, it is judged whether the noise point can be displayed at the current level.

In this embodiment, the basis for judgment is as follows. Energy of the noise point is compared with an energy threshold of the current level. If the energy of the noise point is greater than the energy threshold, the noise point can be displayed; otherwise, the noise point cannot be displayed. In other embodiments, other attributes of the noise point can be compared with other attributes of the system.

In Step 615, the number of the noise points at the level is increased by one.

In Step 616, it is judged whether all pixel points in all of the stored color flow images are traversed. If yes, the procedure proceeds to Step 617; otherwise, Steps 611 to 615 are repeated on a next pixel point.

In Step 617, a noise ratio is calculated.

A specific formula for calculating the noise ratio is the same as that in Step S520.

In Step 618, it is judged whether statistics on all of the levels are completed.

Specifically, it is judged whether noise ratios of all of the levels are calculated. If not, the method proceeds to Step 619. If the statistics on all of the levels are completed, the procedure proceeds to Step 620.

In Step 619, the current level is decreased by one, and Steps 611 to 618 are repeated.

In Step 620, the corresponding noise ratios of all of the levels are compared with the preset noise threshold to acquire a noise ratio closest to the preset noise threshold, and a level corresponding to the noise ratio is selected.

The level closest to the preset noise threshold acquired through Steps 601 to 620 is used as a noise gain level, and the system automatically adjusts the color gain according to the level.

In another embodiment, color gain is controlled by controlling a ratio of the number of color flow points that are allowed to overflow out of walls of a blood vessel in a sampling frame to a non-overflow flow space in the sampling frame. A method may include the following steps.

In Step A2, color gain is adjusted to a preset level to display overflow points as much as possible.

In Step B2, a speed, a variance, and an energy of each image pixel point and a brightness value of a two-dimensional monochrome image are taken and are used as a basis for judgment.

In Step C2, if a speed of an image pixel point is greater than a preset overflow speed threshold value, energy of the image pixel point is greater than a preset overflow energy threshold value, and a corresponding two-dimensional image point brightness value is greater than a preset brightness threshold value, the point is regarded as an overflow point.

In Step D2, if a speed of a pixel point is greater than the preset overflow speed threshold value, an energy of the pixel point is greater than the preset overflow energy threshold value, and a corresponding two-dimensional image point brightness value is less than the preset brightness threshold value, the point is regarded as a non-overflow point.

In Step E2, according to each gain level built into a system, an energy threshold corresponding to the gain level is acquired.

In Step F2, whether an overflow point signal can be displayed at the level is judged according to the energy threshold of the gain level.

In Step G2, an overflow ratio is calculated.

In Step H2, a gain level corresponding to an overflow ratio closest to a preset overflow threshold is acquired according to the preset overflow threshold, and the system performs an automatic adjustment according to the gain level.

Figure 7:
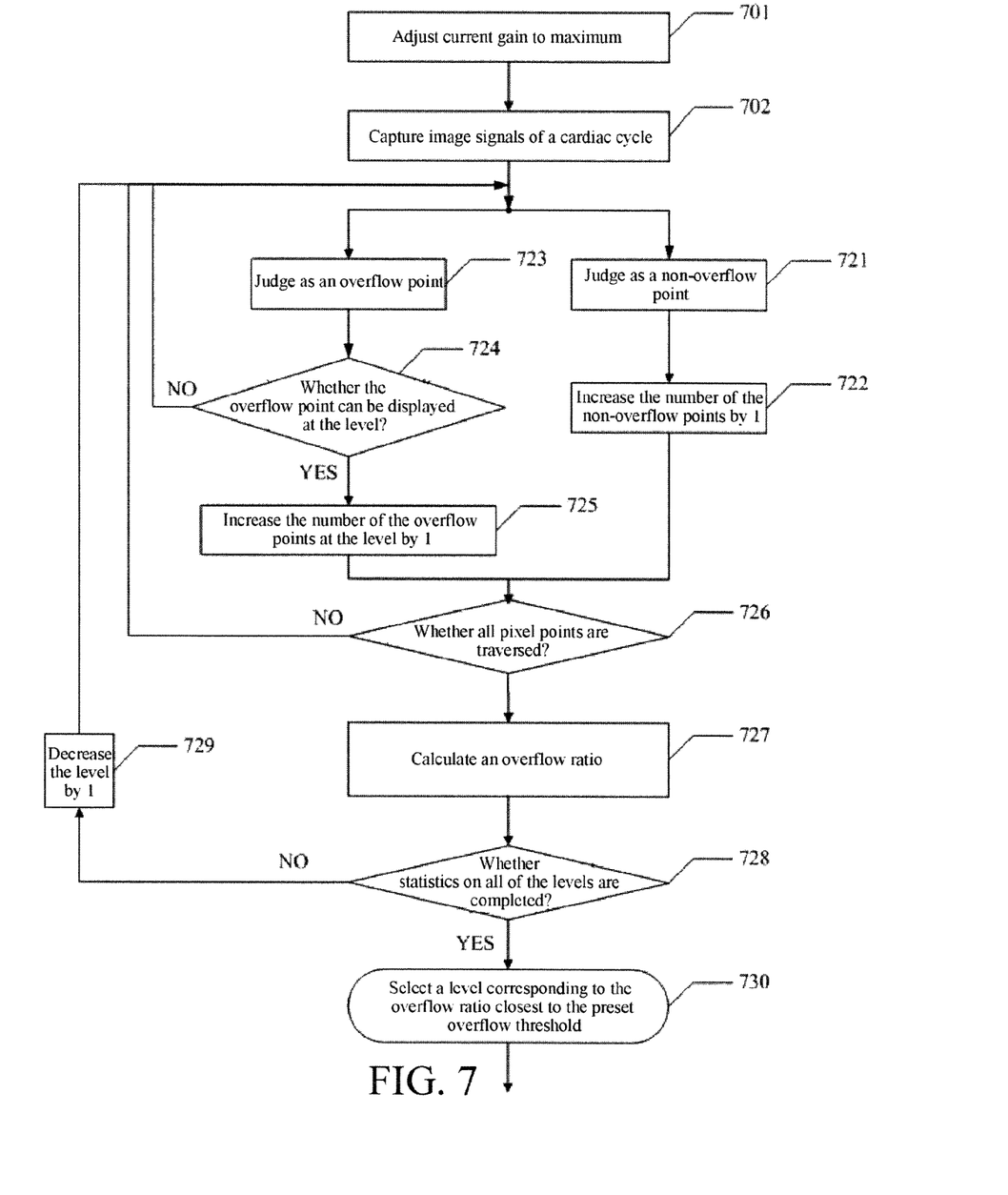
FIG. 7 is a schematic flow chart of suppressing noise according to the embodiment shown in FIG. 5.
Figure 8:
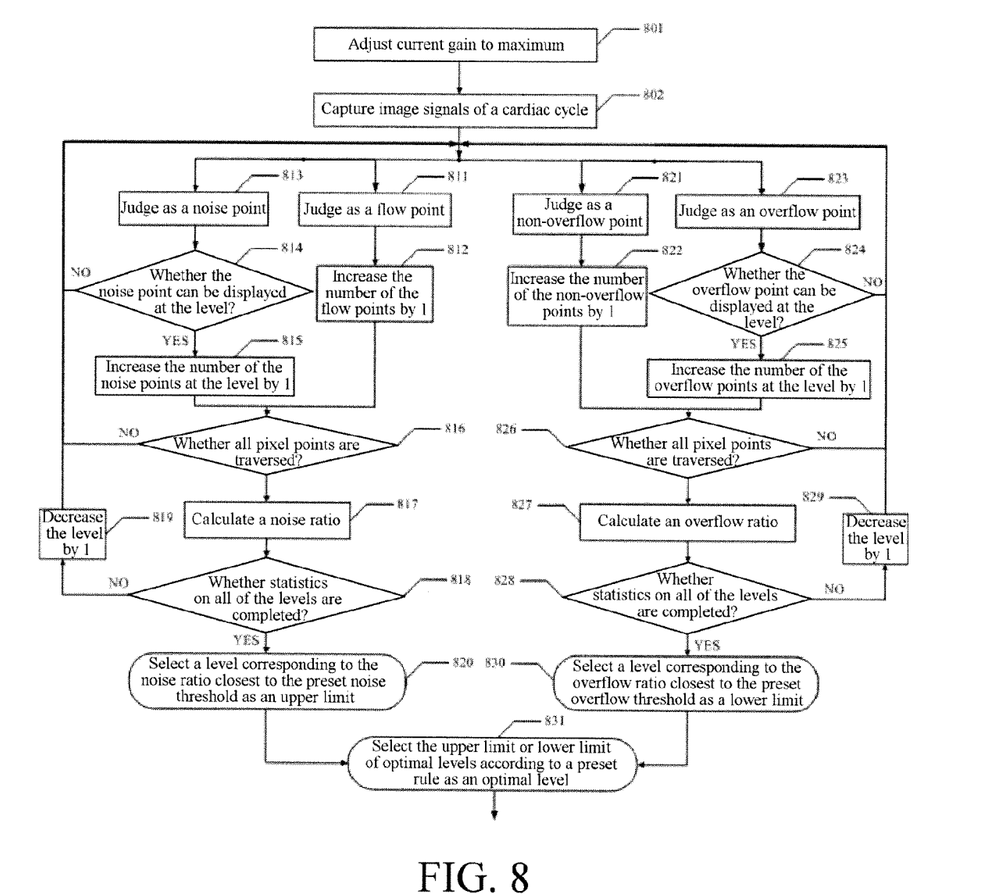
FIG. 8 is a schematic flow chart of suppressing overflows and noise at the same time according to the embodiment shown in FIG. 5.

As shown in FIG. 7, an embodiment includes the following steps.

Steps 701 to 702 are the same as Steps 601 to 602, and are not described again herein.

In Step 721, a pixel point of a stored color flow image is judged as a non-overflow point.

A specific judgment method is the same as that in Step S520.

In Step 722, the number of the non-overflow points is increased by one.

In Step 723, a pixel point of the stored color flow image is judged as an overflow point.

In Step 724, it is judged whether the overflow point can be shown at the current level.

In this embodiment, the basis for judgment is as follows. Energy of the overflow point is compared with an energy threshold of the current level. If the energy of the overflow point is greater than the energy threshold, the overflow point can be displayed; otherwise, the overflow point cannot be displayed. In other embodiments, other attributes of the noise point can be compared with other attributes of the system.

In Step 725, the number of the overflow points at the level is increased by one.

In Step 726, it is judged whether all pixel points in all of the stored color flow images are traversed. If yes, the procedure proceeds to Step 727; otherwise, Steps 721 to 725 are repeated on a next pixel point.

In Step 727, an overflow ratio is calculated.

A specific formula for calculating the overflow ratio is the same as that in Step S520.

In Step 728, it is judged whether statistics on all of the levels are completed.

Specifically, it is judged whether overflow ratios of all of the levels are calculated. If not, the procedure proceeds to Step 729. If the statistics on all of the levels are completed, the procedure proceeds to Step 730.

In Step 729, the current level is decreased by one, and Steps 721 to 728 are repeated.

In Step 730, the corresponding overflow ratios of all of the levels are compared with the preset overflow threshold to acquire an overflow ratio closest to the preset overflow threshold, and a level corresponding to the overflow ratio is selected.

The level closest to the preset overflow threshold acquired through Steps 701 to 730 is used as an overflow gain level, and the system automatically adjusts the color gain according to the level.

In yet another embodiment, an upper limit of color gain is determined by limiting the number of noise points in a sampling frame and a lower limit of color gain is determined by limiting a color overflow degree in the sampling frame, so that a suitable color gain level is determined. As shown in FIG. 8, the embodiment includes the following steps.

Steps 801 to 802 are the same as Steps 601 to 602, and are not described again herein.

Steps 811 to 820 are the same as Steps 611 to 620, and an acquired noise gain level is used as an upper limit of optimal gain levels for output.

Similarly, Steps 821 to 830 are the same as Steps 721 to 730, and an acquired overflow gain level is used as a lower limit of the optimal gain levels for output.

In Step 830, an optimal gain level is selected between the upper limit and the lower limit of the optimal gain levels according to a preset rule, and the system automatically adjusts the color gain according to the optimal gain level.

After the upper limit and the lower limit of the optimal gain levels are calculated, the upper limit, the lower limit, or a specific level value between the upper and lower limits is selected according to actual needs of the mode used by a user. For example, in a carotid mode that is sensitive to overflow, the lower limit of the optimal gain levels may be selected as an output level. For example, when a Transcranial Doppler (TCD) mode is used, attention is paid to sensitivity, so that, in this case, the upper limit of the optimal gain levels may be selected as an output level. For example, in a cardiac flow mode, both sensitivity and overflow need to be considered. In this case, a level between the upper limit and the lower limit can be selected as an optimal level for output according to the preset rule. In this embodiment, the preset rule is a preset percentage; that is, according to the preset percentage, a level between the upper and lower limits is selected as an optimal level for output. The system then automatically adjusts the color gain according to the level.

In some embodiments, the gain level is used as an adjustment unit and is increased or decreased to determine the optimal gain level, after which the gain is automatically adjusted according to the optimal gain level. It should be understood by persons skilled in the art that, according to concepts disclosed herein, a certain gain step may also be used as the adjustment unit to increase or decrease the gain value, so as to determine an optimal gain value directly.

The disclosed techniques cannot only be used to perform automatic optimization of gain in real time without interrupting the normal diagnosis of a doctor, but also can be used to achieve automatic optimization of gain when a demand for automatic optimization is triggered externally. For example, the system may be disposed with a functional button such, as "one-touch gain optimization" button, and the function of the button is achieved by using the embodiments of the present disclosure, so that a user can trigger automatic optimization of gain by pressing the functional button.

In the color flow gain adjustment method according to the present disclosure, an ultrasonic signal is transmitted and received, and a received ultrasonic Doppler signal is processed to acquire color flow image data and two-dimensional monochrome image data. In a preset time, the color flow image data is processed in real time according to a preset color gain level to acquire at least one frame of color flow image data and at least one frame of two-dimensional monochrome image data. At least one frame of color flow image data can represent a speed, energy, or variance value of the ultrasonic Doppler signal, and at least one frame of two-dimensional monochrome image data can represent two-dimensional distribution of the intensity of tissue echoes of the ultrasonic Doppler signal. Based on preset parameters, the color flow image data and the two-dimensional monochrome image data are analyzed, and color gain is adjusted automatically according to an analysis result.

Based on current color image data, sensitivity of the current color image is provided for, while background noise in a color frame is suppressed and color overflow is controlled. By limiting the number of noise points in the color frame, an upper limit of the color gain is determined, and by limiting a degree of color overflow, a lower limit of the color gain is determined, so that a suitable level is determined for the color gain. In this way, the system can be implemented by using fewer resources, and only a time of a cardiac cycle is required. The system is stable, simplifies manual gain adjustment for a clinician, helps diagnosis of the clinician, and improves diagnosis efficiency. In addition, the system does not optimize speed levels automatically, thereby solving the problem of low-speed flow sensitivity deficiency in the prior art.

The embodiments of the present disclosure may also be applied in B-flow and E-flow based on autocorrelation/cross-correlation algorithms to implement gain and overflow control on calculated flow images. After minor modifications, the embodiments of the present disclosure may also be used in the Tissue Doppler Imaging (TDI) technology to implement gain and overflow control.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray Discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A color flow gain adjustment method, comprising:
    storing ultrasound image data within a preset time;
    calculating an abnormal pixel point ratio in a selected area of the stored ultrasound image data using one of three algorithms; and
    adjusting color gain based on a result of comparing the abnormal pixel point ratio and a preset threshold;
    wherein a first of the three algorithms comprises calculating the abnormal pixel point ratio based on the total number of abnormal pixel points in the selected area divided by the total number of pixel points in the selected area,
    wherein a second of the three algorithms comprises calculating the abnormal pixel point ratio based on the total number of abnormal pixel points in the selected area divided by the difference between the total number of pixel points in the selected area and the total number of normal pixel points in the selected area, and
    wherein a third of the three algorithms comprises calculating the abnormal pixel point ratio based on the total number of abnormal pixel points in the selected area divided by the total number of normal pixel points in the selected area.

2. The color flow gain adjustment method according to claim 1,
    wherein calculating the abnormal pixel point ratio in the selected area of the stored ultrasound image data comprises:
    judging abnormal pixel points in the selected area of the ultrasound image data according to preset threshold values on each gain level built into a system based on the ultrasound image data; and
    calculating the abnormal pixel point ratio according to judged abnormal pixel points, so as to acquire the abnormal pixel point ratio corresponding to each of the gain levels built into the system;
    wherein adjusting the color gain based comprises: comparing the abnormal pixel point ratio with the preset threshold, selecting a maximum abnormal pixel point ratio from abnormal pixel point ratios smaller than the preset threshold, and performing the color gain adjustment according to a gain level corresponding to the maximum abnormal pixel point ratio;
    wherein the preset threshold values comprise a speed threshold value, an energy threshold value, a brightness threshold value, and/or a variance threshold value, and judging the abnormal pixel points in the ultrasound image data according to the preset threshold values comprises:
    determining a speed, energy, brightness, and/or variance of each pixel point in the selected area of the ultrasound image data; and
    comparing the speed, energy, brightness, and/or variance of each of the pixel points with the speed threshold value, energy threshold value, brightness threshold value, and/or variance threshold value, respectively, and judging whether the pixel point is an abnormal pixel point according to a comparison result.

3. The color flow gain adjustment method according to claim 2, wherein the abnormal pixel points comprise overflow points and/or noise points, and the abnormal pixel point ratios comprise an overflow ratio and/or a noise ratio.

4. The color flow gain adjustment method according to claim 3, wherein the speed threshold value comprises an overflow speed threshold value and the energy threshold value comprises an overflow energy threshold value, and
    wherein, if a speed of a pixel point is greater than the overflow speed threshold value, an energy of the pixel point is greater than the overflow energy threshold value, and a brightness of the pixel point is greater than the brightness threshold value, the pixel point is judged as an overflow point.

5. The color flow gain adjustment method according to claim 3, wherein the speed threshold value comprises a noise speed threshold value, the energy threshold value comprises a noise energy threshold value, and the variance threshold value comprises a noise variance threshold value, and
    wherein, if a speed of a pixel point is greater than the noise speed threshold value, an energy of the pixel point is less than the noise energy threshold value, and a variance of the pixel point is greater than the noise variance threshold value, the pixel point is judged as a noise point.

6. The color flow gain adjustment method according to claim 3, wherein the abnormal pixel point ratio comprises an overflow ratio and a noise ratio, the preset threshold comprises an overflow threshold and a noise threshold; and wherein adjusting the color gain comprises:
    comparing the overflow ratio with the overflow threshold;
    selecting a maximum overflow ratio from overflow ratios smaller than the overflow threshold;
    using a gain level corresponding to the overflow ratio as a lower limit of optimal gain levels;
    comparing the noise ratio with the noise threshold;
    selecting a maximum noise ratio from noise ratios smaller than the noise threshold;
    using a gain level corresponding to the noise ratio as an upper limit of the optimal gain levels; and
    selecting a gain level between the lower limit of the optimal gain levels and the upper limit of the optimal gain levels to perform the color gain adjustment.

7. The color flow gain adjustment method according to claim 2, further comprising:
    comparing the speed, energy, brightness, and/or variance of each of the pixel points with the speed threshold value, energy threshold value, brightness threshold value, and/or variance threshold value, respectively, and judging whether the pixel point is a normal pixel point according to a comparison result; and
    calculating the abnormal pixel point ratio according to the judged abnormal pixel points and normal pixel points so as to acquire the abnormal pixel point ratio corresponding to each of the gain levels built into the system.

8. The color flow gain adjustment method according to claim 7, wherein the abnormal pixel point ratio is $$\text{Abnomal\_ratio} = \frac{N_{abnomal}}{N_{total} - N_{normal}} \text{ or } \text{Abnomal\_ratio} = \frac{N_{abnomal}}{N_{normal}},$$

where Abnomal_ratio is the abnormal pixel point ratio, $N_{total}$ is the total number of pixel points in the selected area, $N_{normal}$ is the total number of normal pixel points in the selected area, and $N_{abnormal}$ is the total number of abnormal pixel points in the selected area.

9. The color flow gain adjustment method according to claim 7, wherein the normal pixel points comprise non-overflow points and/or flow points, the speed threshold value comprises the overflow speed threshold value and/or the noise speed threshold value, the energy threshold value comprises the overflow energy threshold value and/or the noise energy threshold value, and the variance threshold value comprises the noise variance threshold value, and wherein, if a speed of a pixel point is greater than the overflow speed threshold value, an energy of the pixel point is greater than the overflow energy threshold value, and a brightness of the pixel point is less than the brightness threshold value, the pixel point is judged as a non-overflow point; and wherein, if a speed of a pixel point is greater than the noise speed threshold value and a variance of the pixel point is less than the noise variance threshold value, the pixel point is judged as a flow point.

10. The color flow gain adjustment method according to claim 1, wherein the abnormal pixel point ratio is $$\text{Abnomal\_ratio} = \frac{N_{abnomal}}{N_{total}},$$

where Abnomal_ratio is the abnormal pixel point ratio, $N_{total}$ is the total number of pixel points in the selected area, and $N_{abnormal}$ is the total number of abnormal pixel points in the selected area.

11. A color flow gain adjustment device, comprising:
a storage module for storing ultrasound image data within a preset time;
a logic module for calculating an abnormal pixel point ratio in a selected area of the stored ultrasound image data using one of three algorithms; and
an adjustment module for adjusting color gain based on a result of comparing the abnormal pixel point ratio and a preset threshold;
wherein a first of the three algorithms comprises calculating the abnormal pixel point ratio based on the total number of abnormal pixel points in the selected area divided by the total number of pixel points in the selected area,
wherein a second of the three algorithms comprises calculating the abnormal pixel point ratio based on the total number of abnormal pixel points in the selected area divided by the difference between the total number of pixel points in the selected area and the total number of normal pixel points in the selected area, and
wherein a third of the three algorithms comprises calculating the abnormal pixel point ratio based on the total number of abnormal pixel points in the selected area divided by the total number of normal pixel points in the selected area.

12. The color flow gain adjustment device according to claim 11,
wherein the logic module comprises:
an analysis unit for judging abnormal pixel points in the selected area of the ultrasound image data according to preset threshold values on each gain level built into the system based on the ultrasound image data; and
a calculation unit for calculating the abnormal pixel point ratio according to judged abnormal pixel points, so as to acquire the abnormal pixel point ratio corresponding to each of the gain levels built into the system; wherein when the adjustment module adjusts the color gain based on the comparison result, the adjustment module compares the abnormal pixel point ratio with the preset threshold, selects a maximum abnormal pixel point ratio from abnormal pixel point ratios smaller than the preset threshold, and performs the color gain adjustment according to a gain level corresponding to the maximum abnormal pixel point ratio;

wherein the preset threshold values comprise a speed threshold value, an energy threshold value, a brightness threshold value, and/or a variance threshold value; and wherein the analysis unit comprises:

an acquiring subunit for determining a speed, energy, brightness and/or variance of each pixel point in the selected area of the ultrasound image data; and a judgment subunit for comparing the speed, energy, brightness, and/or variance of each of the pixel points with the speed threshold value, energy threshold value, brightness threshold value, and/or variance threshold value, respectively, and judging whether the pixel point is an abnormal pixel point according to a comparison result.

13. The color flow gain adjustment device according to claim 12, wherein the abnormal pixel points comprise overflow points and/or noise points, and the abnormal pixel point ratios comprise an overflow ratio and/or a noise ratio.

14. The color flow gain adjustment device according to claim 13, wherein the speed threshold value comprises an overflow speed threshold value and the energy threshold value comprises an overflow energy threshold value, and wherein when the judgment subunit judges that a speed of a pixel point is greater than the overflow speed threshold value, an energy of the pixel point is greater than the overflow energy threshold value, and a brightness of the pixel point is greater than the brightness threshold value, the judgment subunit judges the pixel point as an overflow point.

15. The color flow gain adjustment device according to claim 13, wherein the speed threshold value comprises a noise speed threshold value, the energy threshold value comprises a noise energy threshold value, and the variance threshold value comprises a noise variance threshold value, and wherein when the judgment subunit judges that a speed of a pixel point is greater than the noise speed threshold value, an energy of the pixel point is less than the noise energy threshold value, and a variance of the pixel point is greater than the noise variance threshold value, the judgment subunit judges the pixel point as a noise point.

16. The color flow gain adjustment device according to claim 12, wherein the analysis unit compares the speed, energy, brightness, and/or variance of each of the pixel points with the speed threshold value, energy threshold value, brightness threshold value, and/or variance threshold value, respectively, and judges whether the pixel point is a normal pixel point according to a comparison result; and the calculation unit calculates the abnormal pixel point ratio according to the judged abnormal pixel points and normal pixel points, so as to acquire the abnormal pixel point ratio corresponding to each of the gain levels built into the system.

17. The color flow gain adjustment device according to claim 16, wherein
the abnormal pixel point ratio is $$\text{Abnomal\_ratio} = \frac{N_{abnomal}}{N_{total} - N_{normal}} \text{ or Abnomal\_ratio} = \frac{N_{abnomal}}{N_{normal}},$$

where abnomal_ratio is the abnormal pixel point ratio, $N_{total}$ is the total number of pixel points in the selected area, $N_{normal}$ is the total number of normal pixel points in the selected area, and $N_{abnomal}$ is the total number of abnormal pixel points in the selected area.

18. The color flow gain adjustment device according to claim 16, wherein the normal pixel points comprise non-overflow points and/or flow points, the speed threshold value comprises the overflow speed threshold value and/or the noise speed threshold value, the energy threshold value comprises the overflow energy threshold value and/or the noise energy threshold value, and the variance threshold value comprises the noise variance threshold value, and wherein
when the judgment subunit judges that a speed of a pixel point is greater than the overflow speed threshold value, an energy of the pixel point is greater than the overflow energy threshold value, and a brightness of the pixel point is less than the brightness threshold value, the judgment subunit judges the pixel point as a non-overflow point; and wherein
when the judgment subunit judges that a speed of a pixel point is greater than the noise speed threshold value and a variance of the pixel point is less than the noise variance threshold value, the judgment subunit judges the pixel point as a flow point.

19. The color flow gain adjustment device according to claim 11, wherein the abnormal pixel point ratio is $$\text{Abnomal\_ratio} = \frac{N_{abnomal}}{N_{total}},$$

where Abnomal_ratio is the abnormal pixel point ratio, $N_{total}$ is the total number of pixel points in the selected area, and $N_{abnomal}$ is the total number of abnormal pixel points in the selected area.

20. A color ultrasound imaging system, comprising a transducer and a signal processing device, wherein the transducer is for transmitting an ultrasonic signal and receiving an ultrasonic echo signal and the signal processing device is for performing signal processing on the ultrasonic echo signal received by the transducer to acquire ultrasound image data, the system further comprising a color flow gain adjustment device including:

a storage module for storing ultrasound image data within a preset time;

a logic module for calculating an abnormal pixel point ratio in a selected area of the stored ultrasound image data using one of three algorithms; and an adjustment module for adjusting color gain based on a result of comparing the abnormal pixel point ratio and a preset threshold;

wherein a first of the three algorithms comprises calculating the abnormal pixel point ratio based on the total number of abnormal pixel points in the selected area divided by the total number of pixel points in the selected area, wherein a second of the three algorithms comprises calculating the abnormal pixel point ratio based on the total number of abnormal pixel points in the selected area divided by the difference between the total number of pixel points in the selected area and the total number of normal pixel points in the selected area, and wherein a third of the three algorithms comprises calculating the abnormal pixel point ratio based on the total number of abnormal pixel points in the selected area divided by the total number of normal pixel.

* * * * *